United States Patent [19]

Savage et al.

[11] Patent Number: 5,284,570
[45] Date of Patent: Feb. 8, 1994

[54] FLUID SAMPLE ANALYTE COLLECTOR AND CALIBRATION ASSEMBLY

[75] Inventors: Douglas R. Savage, Del Mar; Ronald E. Betts, La Jolla; Richard J. Koerner, San Diego; Douglas R. Hillier, San Juan Capistrano, all of Calif.

[73] Assignee: PPG Industries, Inc., Pittsburgh, Pa.

[21] Appl. No.: 721,028

[22] Filed: Jun. 26, 1991

[51] Int. Cl.⁵ .................................. G01N 27/26
[52] U.S. Cl. .................... 204/422; 204/403; 204/406; 204/409; 204/412; 204/433; 204/435; 128/635
[58] Field of Search .............. 204/403, 409, 433, 406, 204/416, 435, 412, 422; 128/635, 760, 766; 422/61

[56] References Cited

U.S. PATENT DOCUMENTS

| | | | |
|---|---|---|---|
| Re. 29,656 | 6/1978 | Chittenden et al. | 128/272.3 |
| 2,267,074 | 12/1941 | Brockway | 128/215 |
| 3,000,805 | 9/1961 | Carritt et al. | 204/195 |
| 3,049,118 | 8/1962 | Arthur et al. | 128/2 |
| 3,088,905 | 5/1963 | Glover | 204/195 |
| 3,336,924 | 8/1967 | Sarnoff et al. | 128/272 |
| 3,497,442 | 2/1970 | Vincent | 204/195 |
| 3,681,255 | 8/1972 | Wilfore | 262/408 |
| 3,826,260 | 7/1974 | Killinger | 128/272 |
| 3,912,614 | 10/1975 | Spracklen et al. | 204/195 B |
| 3,940,003 | 2/1976 | Larson | 215/247 |
| 3,977,555 | 8/1976 | Larson | 215/247 |
| 4,059,112 | 11/1977 | Tischlinger | 128/272.3 |
| 4,133,735 | 1/1979 | Afromowitz et al. | 204/195 G |
| 4,339,317 | 6/1982 | Meiattini et al. | 204/195 B |
| 4,454,007 | 6/1984 | Pace | 204/1 T |
| 4,615,340 | 10/1986 | Cronenberg et al. | 128/635 |
| 4,734,184 | 3/1988 | Burleigh et al. | 204/409 |
| 4,863,016 | 9/1989 | Fong et al. | 206/210 |
| 4,886,495 | 12/1989 | Reynolds | 604/88 |
| 4,941,308 | 7/1990 | Grabenkort et al. | 53/425 |
| 4,969,883 | 11/1990 | Gilbert et al. | 604/414 |
| 4,982,740 | 1/1991 | Broden | 128/760 |
| 5,046,496 | 9/1991 | Betts et al. | 204/409 |
| 5,080,865 | 1/1992 | Leiner et al. | 204/409 |
| 5,096,669 | 5/1992 | Lauks et al. | 204/403 |

FOREIGN PATENT DOCUMENTS

0015075 9/1980 European Pat. Off. .
0027385 4/1981 European Pat. Off. .

OTHER PUBLICATIONS

Product Information Sheets on SANCAP material.
MOCON (Modern Controls, Inc.) Product Brochure.
"Medical and Biological Engineering Computing", vol. 16, 1978, pp. 599–600.
"Quality Control in Blood pH and Gas Analysis by Use of a Tonometered Bicarbonate Solution and Duplicate Blood Analysis" *Journal of Clinical Chemistry*, vol. 27, No. 10, 1981, pp. 1761-1763 (Abstract).

*Primary Examiner*—John Niebling
*Assistant Examiner*—Bruce F. Bell
*Attorney, Agent, or Firm*—Kenneth J. Stachel

[57] ABSTRACT

A fluid sample collector, sensing, and calibration device contains a collector like a syringe, with one or more analyte sensors, and a calibrator for calibrating the sensor. These can be pre-assembled and are particularly adapted to be disposable after a single use; the analyte sensor may be connected to a self-contained monitoring instrument or analyzer which processes the signals from the sensor and displays the information to the operator.

39 Claims, 3 Drawing Sheets

FLUID SAMPLE ANALYTE COLLECTOR AND CALIBRATION ASSEMBLY

BACKGROUND OF THE INVENTION

This invention relates to an apparatus with a fluid sample collection device with one or more sensors for the measurement of analytes in conjunction with a calibration assembly or device. More particularly, the present invention relates to such an apparatus that is a portable collector, sensor and calibrator assembly for use with a measurement display means.

Numerous methods and apparatus exist in the art for measuring chemical components or analytes of fluids. For instance, when the fluid is a liquid or liquid with a dissolved gas with or without the presence of solids, it may be necessary with current technology to transport a sample to a location for testing. With centralized testing, the bulky, stationary, elaborate and sophisticated equipment performs the analysis on a practically endless number of samples. An example of this is the qualitative and/or quantitative measurement of constituents or analytes of blood. For instance, the measurement of blood gases, usually a measure of the partial pressures of oxygen and carbon dioxide, along with the pH from a sample of arterial blood gives the state of the acid base balance of the effectiveness of both the respiratory and cardiovascular systems of the human or vertebrate body. For measuring constituents of blood, the blood sample is drawn from the patient and usually, as in the case of blood gases, transported to a central location for testing.

This technique of transporting the sample to stationary measuring equipment can lead to problems. Ingenious technology has broached solutions to maintain the original composition of the fluid during transportation. Elaborate designs for syringes used in taking the blood samples overcame some of the problems that resulted in inaccurate readings of the particular chemical constituent being measured. For instance, for determining blood gas composition, the problem of air contamination in the collected sample was solved by the use of liquid heparin as an anticoagulant. Unfortunately, this introduced a sample dilution problem. Subsequent development resulted in the use of heparin in the dry state as opposed to the liquid state to avoid this dilution. Also, elaborate designs provide for proper mixing of the sample after transportation and before testing. Even with these improvements, there are many reports in the literature that suggest that the values obtained in the measurement of blood gases depend on the type of measuring equipment and the technique for sample collection.

The art also has attempted to develop more portable measuring equipment rather than the fairly expensive nonportable equipment that engender the elaborate and cumbersome transportation techniques. Portable devices would shorten or overcome transporting the sample altogether so that a patient's blood gases could be measured at the bedside in a manner similar to measuring a patient's temperature. U.S. Pat. Nos. 3,000,805 and 3,497,442 show two such devices. The former has electrodes located on a syringe plunger and the latter has electrodes placed in the syringe well to conduct the measurements. The electrodes are the sensing devices for the blood gases. In the allowed United States patent application Ser. No. 07/343,234, assigned to the same assignee as the present application, the applicants describe and claim a portable blood gas sensor which includes electrodes fabricated from a conventional silk screening process where the electrodes are screened on to a ceramic substance. Typically, these electrodes are used along with an electrolyte and analyte permeable membrane that covers the sensor. Some of these membranes may be hydratable membranes that can be stored in a dry state and hydrated just prior to use.

With any device for detecting and measuring the analytes in fluid, the device must be calibrated in some manner to obtain accurate values for the amounts of the analytes in the fluid. In the larger stationary equipment, calibration occurs through the use of reference fluids that are analyzed before and sometimes during the analysis process of the analyte. Such reference fluids can also be used with portable analyte measuring devices but portable devices should be made as user friendly as possible so their use actually can be more portable.

An object of the present invention is to provide a fluid collection and sensor assembly apparatus that has a calibration device. This gives the advantages of: ready-to-use sensors, and assistance in the generation of results in a more timely, accurate and inexpensive manner.

SUMMARY OF THE INVENTION

The foregoing object and others gleaned from the following disclosure are achievable by the present invention. The collector of the present invention is associated with at least one analyte sensor that is also particularly adapted for use with and/or connection to a self-contained, hand-held, preferably battery powered monitoring instrument or analyzer which processes the signals from the sensor and displays the information to the operator.

The fluid collection, sensing and calibrating apparatus, of the present invention has the calibrator, the sensing means, and the collector arranged in fluid communication, where the collector provides for the flow of the calibration fluid from the calibrator to contact the sensing means that is associated with the collector. The calibrator has at least one portion or section that is a base and holder adapted to hold (recess) at least one container of calibration fluid, (preferably the container is held in a vertical fashion). The fluid collector is adapted for fluid communication with the container in the calibrator (needle), where the collector has a body portion defining a chamber at one end and has an actuating means slidable within the body portion at the other end to provide a variable volume for the chamber. At the end of the chamber that is opposite from the actuating means the collector is adapted with connecting means for fluid engagement with means for withdrawing calibration and/or sample fluid. The at least one sensing means is associated with the collector for fluid communication (needle) with the container and in fluid communication with the collection means so that when calibration fluid is withdrawn from the container by the actuating means of the collector and into the chamber the fluid contacts the sensor. This fluid contacting association with the collector is through one or more fluid chambers of the collector itself or with one or more fluid chambers of a distinct sensor assembly in fluid communication with the fluid chamber of the collector. The means for withdrawing calibration fluid is attached to the collector either through the connecting means or through a housing for the sensing means that is affixed for fluid engagement to the collector by the connecting means. The calibration fluid has known levels of one or more analytes for calibrating the one or more sensors. The calibrator may be prepackaged with the collector and sensor for ready use and may be readily disposable.

In one aspect of the present invention the calibrator with the container and the at least one sensing means as a distinct assembly and the collector are attachable for fluid communication in the order recited and along a longitudinal axis for fluid communication from the container to the chamber of the collector. When so engaged, the alignment can be vertical starting at the calibrator to maintain the container in a vertical position during fluid communication to contact the sensing means where the support for the alignment is provided by the holder of the calibrator. This support can be provided by an extended holder that engages at least a portion of the sensing means and/or collector so they are slidable within the holder or by an expanded base of the holder to securely retain the container and the sensing means and collector vertically attached to the container.

Also in this aspect the chamber of the collector and the chamber of the sensing means assembly are separated by a first fluid seal. The first chamber of the collector defines a cylinder and has a piston slidable therein and the actuating means is the means for actuating said piston and also carries a first seal puncturing means. The chamber of the assembly for the sensing means defines a housing that terminates at two ends with connecting means for fluid engagement one for means for withdrawing a sample of fluid and the other with the connecting means of the collector. The connecting means attachment to the chamber of the sensing means defines a connecting conduit for fluid communication. The connecting means or the chamber for connection with the withdrawing means is sealed by a second fluid seal. The calibrator having a body portion defining a cylinder open at one end for slidably receiving at least a portion of said body portion of said collector with the sensing means also has a movable member that carries a second seal puncturing means. This movable member can be slidable in said cylinder of said calibrator to engage the sliding collector and to direct the collector toward the calibration solution in the container at the other end of the calibrator. The puncturing means can be used to puncture the second seal and any seal on the container in the calibrator to allow fluid flow from the container to come in contact with the sensing means and enter into the collector. The sealed container containing calibration solution is located and supported in the end of said cylinder of said calibrator opposite from the opening for the collector with the sensing means.

These, as well as other advantages of the present invention, will become apparent from the following drawings and description of the invention,

DESCRIPTION OF THE INVENTION

Similar numerals are used throughout the drawings to denote similar features in each of the drawings.

Figure 1:
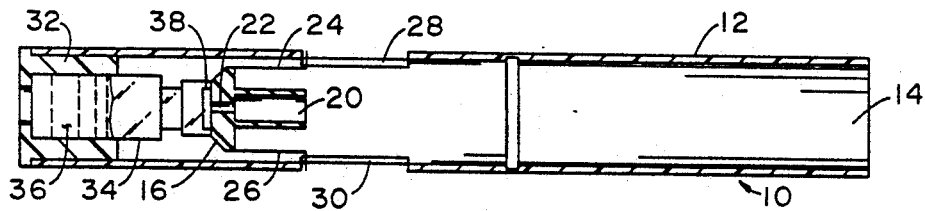
FIG. 1 is a cross sectional view of a calibrator that can be used with various collector designs as shown in FIGS. 2–4 in accordance with the present invention.
Figure 2:
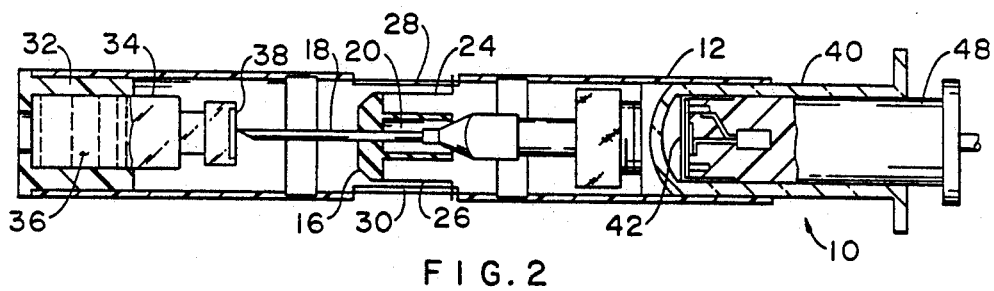
FIGS. 2–4 show the calibrator in use with several different designs for the collector where the collectors are in various states of insertion into the calibrator.

As shown in FIG. 1 a calibrator 10 includes a body portion defining a cylinder 12 having an opening 14 at one end for receiving at least a section of the body portion of any type of collector/sensor, as shown in FIG. 2 as 40. A movable member 16 that is slidable within cylinder 12 is adapted for receiving a seal puncturing means 18, which, for example, may be in the form of a single or double ended, hollow, rigid stainless steel needle. The receipt of the puncturing means 18 is in column space 20 that extends longitudinally from the movable member 16. The member 16 has hole 22 to fixedly engage the needle 18 which can be provided by the calibrator 10 or with a collector/sensor 40. Also the movable member has one or more and preferably two resilient fingers 24 and 26 which resiliently engage slots 28 and 30 provided in the wall of the calibrator 10 to positionally hold the movable member 16 at the start and end point of its travel within the calibrator 10. The travel of the movable member 16 within the cylinder 12 is limited by one or more inwardly facing projections 32 formed on the interior surface of the cylinder 12.

A sealed container 34 containing calibration solution 36, with characteristics that are described infra is supported in the end of the cylinder 12 of the calibrator 10, opposite the opening receiving a collector 40. The container may be a vial with any puncturable cap 38 known to those skilled in the art sealing the mouth of the container 34. Suitable containers depending on the type of calibration fluid include glass vials with an elastomeric stopper or with an induction seal with a snap-cap and plastic containers with similar or different caps or stoppers.

As shown in FIG. 2 a collector generally shown as 40 slidably engages the calibrator 10 through opening 14. The collector can be a standard syringe with a needle where the syringe has one or more sensing means 42 positioned in a chamber at the distal end of the collector 40. Movable member 16 engages the needle 18 of the collector/sensor 40 as it moves toward the vial 34. The needle 18 of the collector/sensor 40 is directed to the piercable top of vial 34 and pierces the top to be in fluid contact with the calibrant 36 in the vial 34. With the collector/sensor 40 in fluid contact with calibrant 36 the plunger 40 is retracted to pull the calibrant through needle 18 into chamber 44 to contact the sensing means 42 to calibrate the sensing means as shown in FIG. 4.

Figure 5:
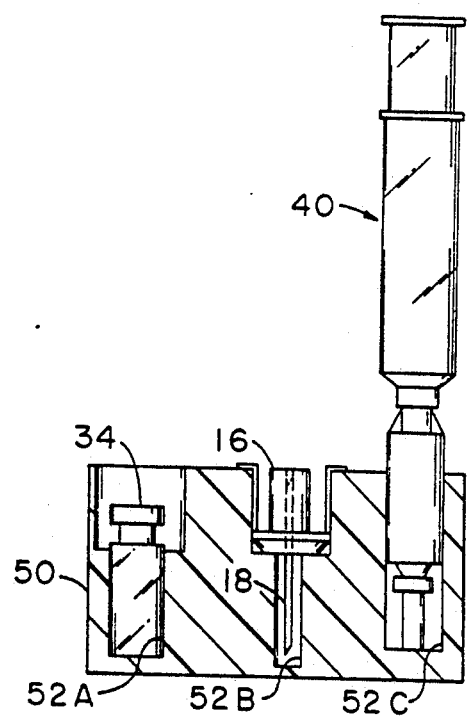
FIG. 5 is a cross sectional view of a calibrator that contains the collector with the sensing means and the puncturing means, which are not shown in cross sectional view, in an original non-vertical arrangement in separate recesses or wells in the calibrator.
Figure 6:
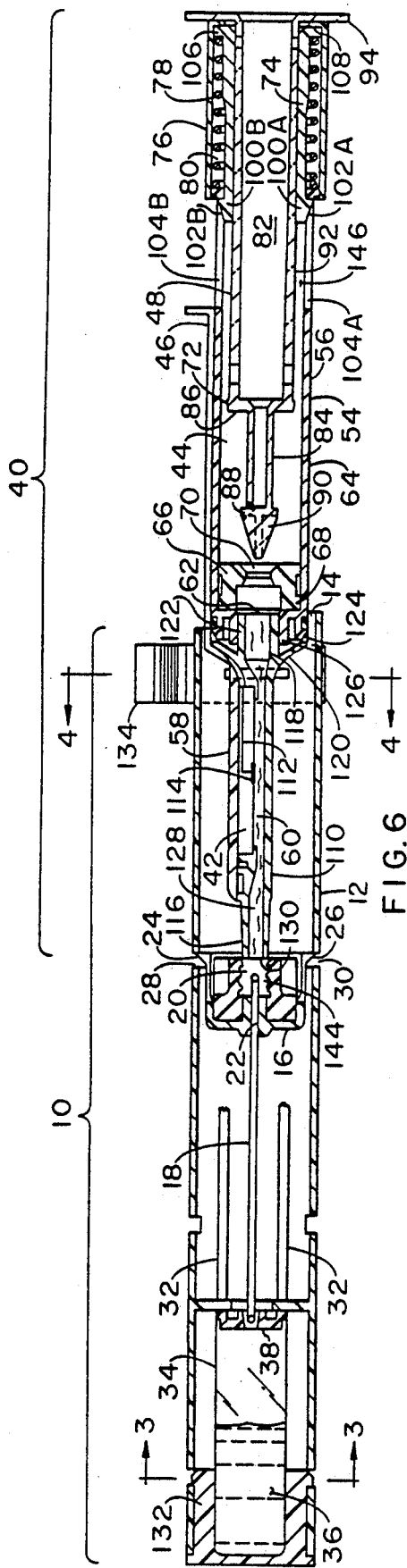
FIG. 6 is a cross sectional view of a syringe and calibrator in accordance with the present invention wherein all of the several seals are intact and unpunctured.

The type of sensing means 42 and the calibration thereof are more fully discussed for FIGS. 5 and 6.

Figure 3:
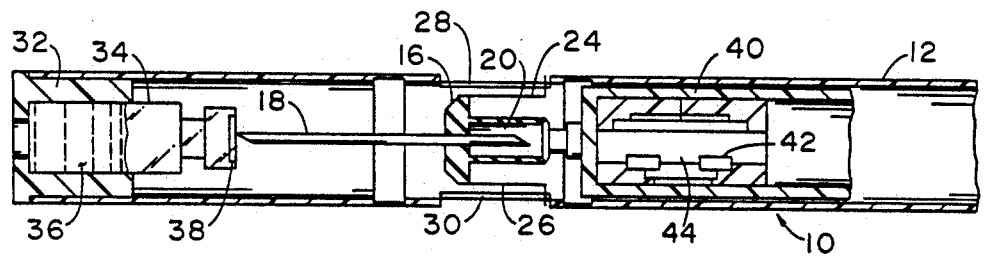
Figure 4:
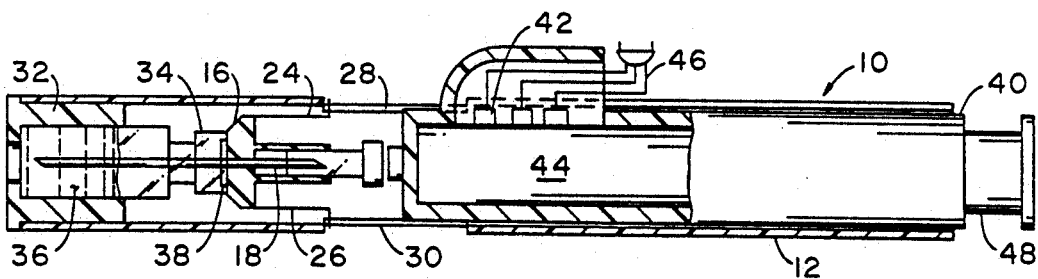

FIGS. 3 and 4 show two different types of collector/sensor 40 engaging movable member 16 where the member 16 has the needle 18 for fixedly engaging the collector to act as the needle for the collector/sensor 40. Also these collector/sensor units can be integral units with the at least one sensing means 42 located in the chamber 44 for a collector like a syringe. The sensing means can be located on the side wall of the syringe-like collector 40 so the sensing means can detect the amount of the analyte in the calibrant and send electrical signals by an electrical cable means 46. The calibration, the collector/sensor 40 can be removed from the calibrator 10 by retraction of a reciprocating actuator 48 of the collector 40. The calibrant 36 can be expelled and sample drawn into the collector/sensor 40 or a larger volume of the sample fluid by several orders of magnitude can be drawn into the collector/sensor 40 with the calibrant still present in the chamber 44 of the collector 40. With this latter approach the at least one sensing means 42 would read the values of the analyte in the sample since the calibrant would be so diluted by the sample.

FIG. 5 depicts an alternative embodiment of the present invention, where the calibrator 10 is a nontubular or noncylindrical device. Here calibrator 10 has a body portion that is a holder 50 having three recesses or wells 52 A, B, and C that extend from a surface of the holder 50 into the holder. These recesses can be parallel or approximately parallel to each other. One recess, for example, 52A holds the calibrant container 34 while another like 52B holds the member 16 and the other 52C holds the collector with the sensing means 40. The recesses can be cylindrical holes in the holder or they can be holes contoured to the matching shape of the object they are to hold. For example the recess 52C for the collector 40 can have a contour to match and accept the contour of the collector where the direction of the contour can be any direction in the holder 50 just so the collector 40 is adequately held be the calibrator 10. This type of calibrator 10 can be used by removing the collector 40 and placing it vertically on top the member 16 for attachment. The member 16 is removed from recess 52B as part of the attached combination of the member 16 and the collector 40. This combination is placed vertically of the container 34 in recess 52A and the piercing member 18 of member 16 is used to at least puncture the seal or cap 38 of the container 34. With the retraction of a reciprocating actuator 48 of the collector 10 the calibrant fluid 36 is drawn to contact the sensing means 42 and into the chamber 44. Any of the collectors 40 depicted in FIGS. 2-7 can be used with this type of calibrator.

Figure 7:
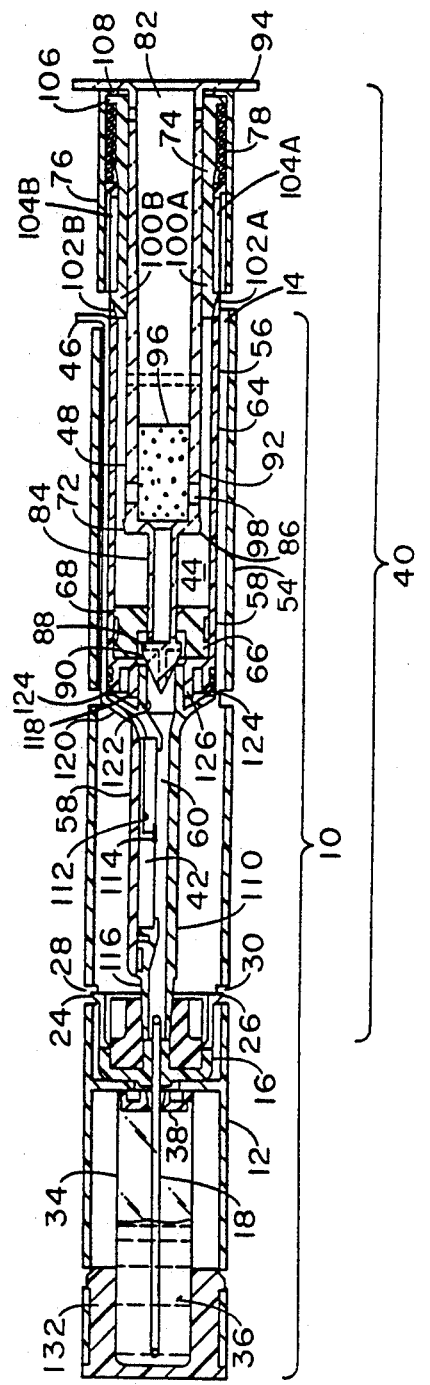
FIG. 7 is a cross sectional view of the syringe and calibrator of FIG. 6 wherein the syringe has been moved with respect to the calibrator; all of the several seals are punctured and the calibration solution may be withdrawn from its container.

Referring now to FIGS. 6 and 7 depicting the preferred embodiment of the present invention, there is shown a fluid sample collection and detection device 40 received in a calibrator 10 in different stages of relative insertion. Device 40 is a sensor/collector that is hereinafter referred to as the "sensor/collector", and the calibration device is hereinafter referred to as the "calibrator". FIG. 6 shows the preferred embodiment of the present invention where the collector 40 is a syringe, and where the sensor/collector/calibrator 40/12 are as they might be in their prepackaged stage of insertion (packaging not shown). FIG. 7 shows the preferred embodiment at the stage of insertion of the sensor/collector 40 into the calibrator 10 just before the withdrawal of the calibration solution 36 from its container 34, all as will be further described below.

The sensor/collector 40 has a body portion 54 comprised of a collector portion 56 and a sensor portion 58. The collector 56 has a first fluid communicating chamber 44 and the sensor portion 58 has a second fluid communicating chamber 60 that other than for a first fluid seal 62 therebetween are juxtaposed for fluid communication between these chambers. The body portion 54 may be made from a suitable plastic material such as a suitable clear styrene plastic.

The first chamber 44 defines a cylinder 64 with a piston 66 slidable therein. The piston 66 is resilient and may be made of plastic or elastomeric material, as for example clear polystyrene or polycarbonate. The piston 66 and the cylinder 64 are circular in cross section and the piston 66 is positioned on a seat 68 provided at one end of the first chamber 44 nearest the second chamber 60. The piston 66 is provided with a centrally disposed, axially extending aperture 70 that has an expanded diameter after an initial narrower diameter to form lip 72.

The piston 66 is actuated by an reciprocating actuator 48 which includes a actuating means 74 reciprocally mounted in a spring biased sleeve 76. The sleeve 76, which may be made of polystyrene or like material known to those skilled in the art, is slidably mounted on the syringe body portion 54.

A spring 78, which may be in the form of a stainless steel helical spring, is disposed in an annular groove 80 in the sleeve 76 and provides a biasing force counter to the slidable movement of the sleeve 76 and its associated actuator toward the piston 66. As an alternative to the spring the reciprocal actuator can be hand operated as indicated in FIGS. 2 and 4, to a mechanical stop or operated pneumatically or with a stepper motor.

The reciprocal actuator 48, which can be a hollow member defining a cavity 82 therein, is provided with a first shaft portion 84 terminating at one end in a raised portion 86 and at the other end in the skirt portion 88 of a first puncturing means, in the form of a puncturing head 90, formed on the end thereof. The reciprocal actuator 48 is further provided with a second shaft portion 92 terminating at one end in a generally planar, annular grasping means 94 and at the other end in the raised portion 86. When the reciprocal actuator 48 allows for venting action, a porous absorbent and expandable material 96, such as white porous polyethylene, can be disposed in the cavity 82 to occlude and retard the venting action upon contact of material 96 with fluid from the chamber 44 that may enter the cavity 82 through aperture 98 provided in the wall of the second shaft portion 92 during operation of the collector 40 and calibrator 10.

As best seen in FIG. 6, the biasing force of the spring maintains a clearance between the seal 62 and the puncturing head 90 of the reciprocal actuator 48 when the collector 40 and calibrator 10 are in their prepackaged stage of insertion. Further, the grasping member 94 of the reciprocal actuator 48 abuts the proximate end of the sleeve 76 and maintains the position of the reciprocal actuator 48 with respect to the spring biased sleeve 76 until overridden by pushing the grasping member 94 and moving the reciprocal actuator 48 into the cylinder 64. The spring biased sleeve 76 is guided, for movement with respect to the collector body portion 54, through resilient fingers 100A and 100B at the end of actuating means 74 that projects into the cylinder 64. These fingers extend in a direction in a parallel plane to the longitudinal axis of cylinder 64 and the walls of cylinder 64. The fingers end in projections 102A and 102B, respectively, that extend outward toward to the wall of cylinder 64. These projections travel in matching longitudinally extending slots 104A and 104B in the wall of the cylinder 64. These slots have a length sufficient to stop the movement of the actuating means 74 at a particular location in the cylinder 64. This distance is that which when translated to the reciprocal actuator 48 through the spring 78 riding on means 74 that connects to sleeve 76 at its proximate end to permit the puncturing head 90 to perforate seal 62 and engage piston 66. The reciprocal actuator 48 can have a range of sliding longitudinal movement within the cylinder 66 before head 90 contacts the piston 66 and before stopping at the proximate end of the cylinder 66. The reciprocal actuator 48 has annular lip 72 at the distal end of second shaft portion 92 to retard the movement of the actuator 48 out of the cylinder 66 at its proximate end. The movement of actuating means 74 out of the cylinder 66 is retarded by projections 102A and 102B of flexible fingers 100A and 100B stopping at the proximate end of longitudinal slots 104A and 104B, respectively. This limitation of movement is translated to the reciprocal actuator 48 by lip 72 abutting the distal end of the actuating means 74 in cylinder 66. The actuating means 74 is attached by one or more and preferably two fastening means 106A and 106B at its proximate end to sleeve 76 at matching fastening means 108A and 108B, respectively. These pairs of fastening means also serve as the proximate boundary for spring 78 within the means 74 and sleeve 76 arrangement. The distal boundary for spring 78 is established by the projections 102A and 102B.

The piston 66 is slidably restrained on the shaft portion 84, by and between the skirt portion 88 and the raised portion 86 for lost motion between the piston 66 and the reciprocal actuator 48, whereby the piston 66 will remain stationary on the shaft portion 84 when not engaged by the skirt portion 88 or the raised portion 86.

The sensing means 42 for body 54 is located in sensor portion or sensor assembly 58 having a housing 110 that can have any basic geometric shape suitable for containing the second fluid communicating chamber 60 and sensing means 42. The sensing means 42 may be in the form of one or more sensors and preferably three sensors with appropriate electrodes as known to those skilled in the art for measuring partial pressure of oxygen and/or carbon dioxide and/or pH of a fluid like blood. Sensing means 42 may be provided with a suitable electric cable means 46 which would have suitable electronic connection fitting (not shown) for connecting the sensing means 42 to a signal processing means (not shown) to process the output signal of the sensing means 42. Cable 46 can be any suitable electronic data communication cable having one or more leads but preferably the cable is a ribbon-type cable with a plurality of wires in one tape-like strip to provide the sensing means 42 with electrical communication from the at least one sensor. The sensing means 42 can be any nonconducting substrate having one or more sensors electrically attached to an electrical circuit means (not shown) as is known to those skilled in the art. Generally, the nonconducting substrate can be a glass or ceramic including sheet or chip or nonconducting substrate like wood or nonconducting polymers or commercially available frit that can be used as the substantially smooth flat surface for the nonconducting substrate. Nonexclusive examples include borosilicate glass as is known to those skilled in the art for producing thick film or layered circuits. A nonexclusive but preferred example of which includes a ceramic base having around 96% Al2O3 such as that available commercially from Coors Ceramic Company, Grand Junction, Colorado. Generally, the electrical circuit means 112 is any electrical circuit means known by those skilled in the art. Both the at least one sensor 114 and the electrical circuit means 114 of the sensing means 42 can be prepared from any number of well known layered circuit or integrated circuit technologies, as for example, thick film, thin film, plating, pressurized laminating and photolithographic etching, and the like, however, the thick film technique is preferred. The sensing means 42 would typically employ sensors, miniature electrodes, or microsensors for measuring analytes, a few nonexclusive examples including: pH, pO2, pCO2 and/or electrolytes in fluids, and in particular blood. The sensor 114 can be a potentiometric or amperometric sensor, in that the former has one electrode and the latter has two, both an anode and a cathode. Such miniature electrodes or microsensors for measuring analytes are known and described in U.S. Pat. Nos. 4,339,317 and 4,615,340 and in the allowed U.S. patent application Ser. No. 07/343,234, filed on Apr. 26, 1989, entitled, "Sensor Assembly for Measuring Analytes in Fluids", which is commonly assigned, all of which are incorporated herein by reference. For a potentiometric sensor an additional electrode is usually present as a reference electrode. Any reference electrode known to those skilled in the art can be used. The potentiometric or amperometric sensor preferably has a hydrophilic polymeric membrane and the sensor preferably has an aqueous-based electrolyte with suitable ionized chemical species. Suitable examples of such membranes that are present in electrochemical sensors for use in determination of blood gases are described in U.S. Pat. Nos. 3,088,905 and 3,912,614 and European patent specifications 0015075 and 0027385 and the article in the journal entitled "Medical and Biological Engineering Computing", 1978, Vol. 16, pages 599-600, all of which are hereby incorporated by reference. The publications describe blood gas detectors requiring the presence of membranes and a number of useful or potentially useful membrane materials. A suitable example of a hydrophilic polymeric membrane shown in the publications is a polyhema. Additionally, polyvinylchloride and modified polyvinylchloride can be used or any hydrophilic hydratable polymeric membrane can be used.

Housing 110 forms at least part of chamber 60 and maintains the sensing means 42 so that its one or more sensors 114 are in fluid contact with chamber 60. Chamber 60 can be comprised of one or more channels having fluid contact with the one or more sensors of sensing means 42. The arrangement of channels and the sensors is such that when a plurality of channels and a plurality of electrodes are present at least one channel of chamber 60 can be in fluid contact with each sensor. Chamber 60 is sealed from the first fluid chamber 44 by the first fluid seal 62. Also housing 110 provides for an electrically insulated electrical attachment of cable 46 to the one or more sensors of the sensing means 42. The housing 110 also provides two openings for chamber 60, where one can be an inlet at connecting conduit 116 and one can be an outlet at the conical expansion 118 of chamber 60. This conical expansion 118 is at the flared end 120 of housing 110. One of these openings is for fluid communication with the first fluid chamber 44 of collector 40 while the other is for fluid communication with the calibrator 10. The conical expansion 118 is formed by housing 110 and is surrounded by flared end 120 which has an inner annular space for fixedly attaching to collector 40. The conical expansion 118 and hub 122 allow for connection or coupling to a device to provide fluid pressure or suction to cause the fluid with the analyte to pass in measuring contact with the one or more sensors of the sensing means 42. Member 118 can be similar to hub 122 or can be adapted and preferably is adapted to connect with a proximate end of a syringe as a collector 40. The conical shape of members 122 and 118 can be of a standard outer diameter to allow for connection to sample gathering means such as needles or tubing or conduit from catheters. Most preferably, the conical shape is suitable for Leur-Lok attachment to a sample gathering means not shown in FIG. 6 such as a needle for a syringe.

The openings of chamber 60 as shown in FIGS. 6 and 7 are preferably aligned in the same plane and along the same axis at opposite ends of chamber 60. In this way chamber 60 passes longitudinally through housing 110 along the same central axis. This arrangement provides sufficient support of the chamber 60 by the housing to receive and/or expel fluid through the chamber 60 with reciprocal movement from the piston 66 on the reciprocal actuator 48 of the collector 40.

The second chamber 60, housing 110 and the centrally disposed hub 122 may be formed integral with the syringe body portion 54 or may and preferably does fixedly attach to the collector body portion 54 by means of interlocking fingers 124 provided on the cup-like end 126 of the collector body portion 54. The fingers each engage a complementary groove provided on the interior surface of the flared end 120 of housing 110. In addition or in lieu of the fingers the housing 110 and body portion 54 may be adhesively connected.

To provide sealed contact between the storage fluid 128 and the sensing means 42, one part of the chamber 60 on each side of the sensing means is sealed so that the fluid 128 is in contact with the one or more sensors of the sensing means 42. Preferably, this sealing is at the inlet and outlet openings of the chamber 60. Preferably, a storage fluid 128 is sealed in the chamber 60 by seal 62 between chambers 60 and 44 and seal 130 and hub 122. Seal 62 preferably is located in chamber 60 after any sensors of the sensing means 42 but before the end of chamber 60 in housing 110 that is close to the collector 40. At the distal end of the sensor assembly 58 from the connection with the collector portion 54, the assembly 58 terminates in a connecting conduit 116 centrally disposed in a hub 122, and this connecting conduit 116 is preferably fluidly sealed by the second fluid seal 130 at or near the end of the conduit.

The calibrator 10 is provided for calibrating the electrode assembly 58 to insure that the measurement of the analytes is accurate. Basically, the calibration of the sensing means 42 involves contacting the sensors of means 42 with a solution of a predetermined analyte value like electrolytes, pH, pO2 and pCO2 values. The outputs of the sensors are measured and calibration coefficients are measured to use with software algorithms, all of which is conventional and known in the art, for example, as described in U.S. Pat. No. 4,734,184.

The calibrator 10 includes a body portion defining a cylinder 12 open at one end 14 for receiving at least a portion of the sensor assembly 58 and/or collector body portion 54. A movable member 16, carrying a second seal puncturing means, which may be in the form of a double ended, hollow, stainless steel needle 18, is slidably received in the cylinder 12. The movably member 16 is provided at least one but preferably two resilient fingers 24 and 26 which resiliently engage slots provided in the wall of the calibrator 10 to positionally hold the movable member 16 at the start and end point of its travel within the calibrator 10. The travel of the movable member 16 within the cylinder 12 is limited by inwardly facing projections 32 formed on the interior surface of the cylinder 12.

Figure 8:
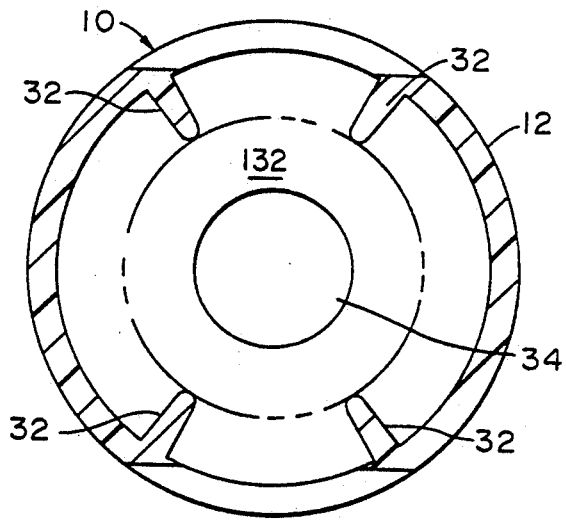
FIG. 8 is a cross sectional view of the calibrator of FIG. 6 along line 3—3 at at the end retaining the container of calibration fluid.

A sealed container 34 containing calibration solution is supported in the end of the cylinder 70 of the calibrator 12, opposite the opening for receiving the sensor collector unit 40 in a similar manner as shown for FIGS. 1 through 4. If container 34 is plastic when the calibration fluid is used as a standard for the analysis of gases in a fluid, the plastic container can be coated with a suitable barrier coating to essentially eliminate any O2 of CO2 permeability of the plastic container to retain the integrity of the calibration solution. The container 34 preferably is seated and centrally received in a cup member 132 that is centrally aligned in the calibrator 10 by a plurality of inwardly facing projections 32 formed in the interior surface of the cylinder 12. The cup member 132 may be made from a suitable plastic material and is sealingly received by the cylinder 12 of calibrator 10. This arrangement is shown in a cross-sectional view in FIG. 8.

The calibration fluid 36 contained in container 34 and the storage fluid 128 contained in the second fluid communicating chamber 60 and possibly in the connecting conduit 116 to be in fluid communication with the one or more sensors can be an analyte-containing fluid as aforementioned. Alternatively the storage fluid 128 can be preferably is an activating fluid. An activating fluid can equilibrate with the one or more sensors that are in an active state in the sensor assembly in order to precondition an active sensor. The analyte-containing fluid can be a gas, liquid or combination of a gas and liquid depending on the state of the analyte that is to be detected by the sensor. For a nonexclusive example, when the analyte is a blood gas such as oxygen and/or carbon dioxide, the storage fluid as an analyte-containing fluid 128 can be a gas. One or more of these gases alone or in combination with each other or with inert gases can purge the second fluid communicating chamber 60 after the sensor assembly 58 has one seal in or over an opening of the chamber 60. After the purging, the second seal is sealed over the unsealed opening of the chamber 60. When the analyte-containing fluid is a combination of gas and a liquid, such a fluid can be produced with the requisite quantity of the gas by any method known to those skilled in the art. For example, such a fluid can be a tonometered fluid produced by any of the commercially available tonometers like the one available from Instrumentation Laboratory under the designation IL237 or by any method known to those skilled in the art like the techniques shown in preparing tonometered buffered solution or whole blood described in the article entitled "Quality Control in Blood pH and Gas Analysis by Use of a Tonometered Bicarbonate Solution and Duplicate Blood Analysis in Clinical Chemistry", Vol. 27, No. 10, 1981 pages 1761-1763, the description of which is hereby incorporated by reference. For such fluids the liquid can be an aqueous solution that is buffered and contains oxygen and carbon dioxide for use in blood gas measurements. Such solutions can be prepared in accordance with U.S. Pat. No. 3,681,255, the description of which is hereby incorporated by reference.

An example of an equilibrated or tonometered fluid as fluid can result from contact of the buffered liquid solution with the carbon dioxide containing gas which can include a mixture of carbon dioxide with one or more inert gases. An inert gas is one which does not react with the buffer solution to change the pH. This would destroy the predictability of a final pH value. Also, inert gas is one that does not react with any of the ingredients in the calibration fluid 34 or storage fluid 128. Nonexclusive examples of inert gases are nitrogen, argon and other similar gases normally found in the air. This includes the noble gases such as neon, argon, krypton, xenon, helium and the like. It is preferred to use as the equilibrating gases for blood gas analysis a mixture of carbon dioxide and nitrogen or carbon dioxide with oxygen and nitrogen. Two nonexclusive examples include: 1) around 5 percent carbon dioxide with oxygen making up the balance of the gas in the fluid, and 2) around 7 volume percent carbon dioxide and around 10 volume percent oxygen and the balance is nitrogen.

For storage fluid 128 that is activating fluid for thick film sensors with one or more hydratable membranes, it is most preferred that this fluid is a hydrating fluid which is chiefly an aqueous fluid with an effective composition to hydrate at least to a partial degree but better to a substantial degree the hydrophilic polymeric membranes. Some sensors with hydratable membranes may be stored dry but they need the hydration of their membranes for the existence of an active state. When the sensor assembly 58 has at least one such sensor, the storage fluid 128 is the activating fluid. Storage fluid 128 is in fluid contact with the sensor by the sealed presence of the fluid in chamber 60. When fluid 128 is hydrating fluid, which it preferably is, any liquid suitable for maintaining the membrane of the one or more sensors 114 in a non-dried state. For instance, the liquid will have some amount of water although a minor quantity of organic liquids may also be present. Preferably, the liquid is a stable liquid for storage ranging from a short time (days or weeks) to prolonged periods of time of several months. Preferably, the liquid is an aqueous solution that is isotonic with any electrolyte in the one or more sensors. More preferably, the fluid 128 as a hydrating is also isotonic to act as the electrolyte for any reference electrodes that may be present in the sensor assembly 58. A suitable example of a hydraulic fluid is an aqueous solution of salts. The quantity of hydrating fluid in chamber 60 or any plurality of channels associated with chamber 60 is at least that which is sufficient to cover or remain in contact with the one or more sensors. Generally, the storage fluid 128 usually does but may not completely fill the chamber 60 of the housing. A nonexclusive example of a suitable process for placing the requisite quantity of analyte-containing or activating fluid 128 in contact with the sensor assembly 58 occurs in the following manner.

One of the openings of the chamber 60 is sealed which can be either the opening sealed with seal 62 or the one sealed with seal 130 by a heat sealing but preferably an induction sealing process. After the sealing of one end, the storage fluid 128 is added to chamber 60 and any side channels that may be present to fill substantially all of the channels although small amounts of air bubbles can be tolerated in the channels but preferably the channels are filled to capacity. The remaining opening of the housing is sealed with the other seal through a heat sealing process but preferably an induction sealing process. In general, the sealing needs to overcome the hurdle of adhering the seal to a plastic or polymeric substrate in a possibly moist environment since there may be moisture or liquid on the surfaces of the housing and vial after the addition of the fluid. In general, however, satisfactory results are obtained by conducting the heat sealing at a temperature higher than the softening or melting point of the heat sealable resin and the pressure is sufficient if it doesn't cause excessive or substantial flow of heat sealable resin away from the area to be sealed.

The seals 38, 62 and 130 may be in the form of a rubber, plastic, or metal foil and adhesive seals that are at least impervious to liquids and preferably substantially impervious to gaseous fluids. For measurement of gaseous analytes the seals are preferably substantially impervious to gas. These seals preferably have at least has two layers—on layer referred to as the "a" layer is away from the mouth or opening of the chamber 60 or vial 34 and another layer referred to as the "b" layer that is in contact with the housing 110 to seal the openings of the chamber 60. The "a" layer can be at least an impervious metal foil, preferably aluminum, and the "b" layer can be one or more adhesive materials. In addition, there may be additional layers on top of the metal foil layer or additional adhesive layers. A suitable example is a paper-backed aluminum foil coated with a clear heater RF (radio frequency) sealable coating. The coating is preferably a blend of a high molecular weight ethylene and vinyl acetate copolymer, available under the trade designation "SANCAP" available from Sancap, 161 Armor Street NE, Alliance, Ohio 44601 for seal 38. For seals 62 and 130 a suitable material is a paper-backed aluminum foil coated with a clear heat sealable coating. The coating is preferably a blend of a high molecular weight ethylene and vinyl acetate copolymer, available under the trade designation "FOIL-SEAL 3-6" available from Selig Sealing Products, Inc., Butterfield Road, Oakbrook Terrace, Ill 60181. Such materials have a gas transmission for oxygen that is nil and a water vapor transmission which ranges from 0.005 to 0.059 GS (grams)/CSI(100in2)/24 hours at 90 percent relative humidity. Such materials provide a seal that when securely attached across the openings provide substantial impervious to air. These values are obtained on a Permatran-W6 for water transmission and an Ox-tran 1000 for oxygen transmission, and both pieces of equipment are available from Mocon, Modern Controls, Inc., 4220 Shingle Creek Parkway, Minneapolis, Minnesota 55430. The thickness of the seals 38, 62 and 130 can range from an overall thickness of around 1 to 10 mils with the heat seal coating ranging in thickness from around 0.5 to around 4 mils and more preferably from around 0.5 to around 2 mils and the aluminum foil ranging in thickness from around 0.1 to around 8 and more preferably from around 0.3 to around 2 mils.

Alternatively, seals 38, 62 and 130 can have an adhesive material as a layer that is one or more thermoplastic resins suitable for hot melt deposition or extrusion lamination. Suitable examples of these thermoplastic resins include resins known as the so-called hot-melt type adhesive, such as polyethylene, an ethylene/vinyl acetate copolymer (EVA) or a partially saponified EVA. For instance, a graft copolymer can be used that is a 20 to 60 percent saponification product of an ethylene/vinyl acetate copolymer (EVA) having a vinyl acetate content of 15 to 45 percent by weight as a trunk polymer and a polymer of an unsaturated carboxylated acid in a quantity of 0.1 to 10 percent by weight of the partially saponified EVA as a branch polymer. Also, the seals 38, 62 and 130 can be a composite of an aluminum/polypropylene film with a heat sealable resin such as a polyamide, polyolefin, and saturated polyesters.

When sealing to adhere the seals to the plastic surface of the housing 110 or the glass or plastic surface with a barrier coating of the container 34 is performed by heat sealing, any induction sealing or any heat sealing method known to those skilled in the art can be used. The method of sealing depends aluminum/polypropylene film with a heat sealable resin such as a polyamide, polyolefin, and saturated polyesters.

The shape of the seal is any geometric configuration that completely covers the openings and provides for a snug fit with the flat surfaces. Preferably, the seal is in the form of a disc having a diameter similar to the diameter across chamber 18 with the housing 110 that surrounds the openings and across the opening and rim of vial 34.

Figure 9:
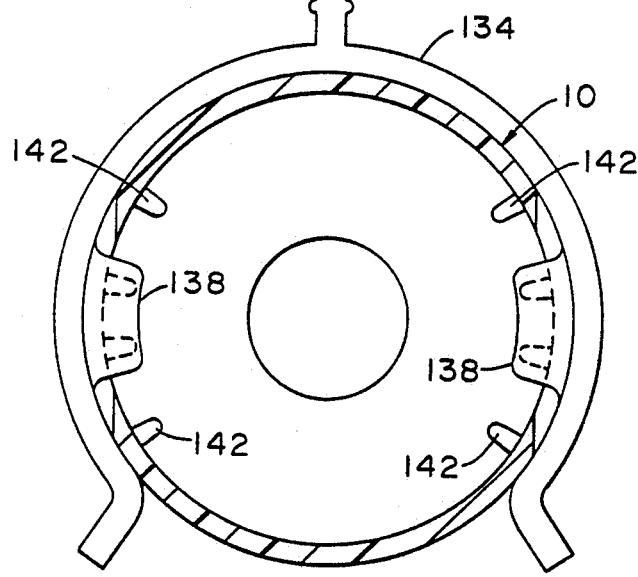
FIG. 9 is a cross sectional view of the calibrator and collector with the sensing means of FIG. 6 along line 4—4 where they are held together in a longitudinal alignment by a fastening means.

The calibrator 10 may also be provided with clamping means 134 which may be in the form of a substantially C-shaped clamp which clampingly engages at least portion of the exterior surface of the calibrator 10. As shown in FIG. 9, the clamp 134 includes a outwardly grasping means 136 outwardly projecting from substantially C-shaped portion of the clamp 134 for grasping and positionally holding the calibrator by the operator. The clamp 134 also includes a plurality of inwardly facing projections 138 formed on the interior surface of the substantially C-shaped portion of the clamp 134 and in registration with a plurality of slots 140 provided in the wall of the calibrator 10 for centrally aligning the sensor collector 40 with respect to said calibrator 10 such that the longitudinal axis of the sensor collector 40 is coincident with the longitudinal axis of the calibrator 10. Additional inwardly facing projections 142 may be formed on the interior surface of the cylinder 12 to further assist in aligning said sensor/syringe 40 with respect to said calibrator 10.

The above description of the sensor/collector 40 and calibrator 10, as before mentioned, is the stage of relative insertion during the prepackaged state. When this assembly is removed from its package, it will be connected to the associated monitoring device by means of the connecting cable 46. At this point the stages that will now occur can be described as: (i) puncture the several seals 38, 62 and 130; (ii) aspirate the calibration solution from the container 34; (iii) remove the calibrator 10 from the sensor/syringe 40; (iv) attach a hypodermic needle or catheter, and (v) draw blood. FIGS. 6 and 7 illustrate steps (i) and (ii) and the remaining steps require no further illustrations.

As can be best seen in FIG. 7., the sensor/syringe 40 and the calibrator 10 are progressively moved, one relative to the other, the puncturing of the first fluid seal 62, the second fluid seal 130 and the seal 38 of the sealed container 76 containing calibration solution occurs. Additionally the container 34 can have a cap 39 covering the seal 38, and the cap can be metal like aluminum of a plastic snap-cap.

To initiate this action, the sleeve 76 and the actuator 74 are moved as a unit by the operator toward the piston 66 until the puncturing head 90 is urged into and through the aperture 70 in the piston 66. The piston is now captured on the reciprocal actuator 48, for movement therewith, by the skirt portion 88 thereof. Concurrently with this movement, the sensor/syringe 40 is progressively moved relative to the calibrator 10 and the hub portion 122, projecting from the syringe body portion 54, is received in centrally disposed cavity 144 in the movable member 16. A portion of the needle 18 punctures the second fluid seal 130 provided at the end of the conduit 116. The so engaged movable member 16, carrying the needle 18, is urged toward the container 34 by the movement of the sensor/collector 40 until the other end of the double-ended needle 18 punctures the seal 38 of the container 34.

At this point in the operation of the assembly, there is fluid communication from the container 34 through the needle 18, conduit 116, second fluid chamber 60 and the first fluid chamber 44 and the calibration solution may be withdrawn from the container 76.

The above described movement of the sleeve 76, to engage the piston 66, compressed spring 78 and now the operator has to merely release the sleeve 76 and the energy stored in the spring 78 will return the sleeve 76, the actuating means 74 and reciprocal actuator 48 to their original position. Such movement of the actuator 48 will move the captured piston 66 a first incremental distance in the first fluid chamber 44 to aspirate or withdraw the calibration solution from the container 34 into the second fluid chamber 60 and into intimate contact with the one or more sensors 114. After the calibration of the one or more sensors 114 is achieved, the operator removes the sensor/syringe 40 from the calibrator 10 and attaches a hypodermic needle or an catheter (not shown) to the sensor/syringe 40 at its hub 116 for drawing the blood sample.

To take the blood sample, the operator then grasps the generally planar, annular grasping portion 94 provided at the end of the actuator 48 and pulls the actuator 48 from the sleeve 76 with enough force to dislodge the abutment of an annular rib 146 that may be located on the second shaft portion 92 with the end of the actuating means 74. This movement of the actuator 48 moves the captured piston 66 a second incremental distance in the first fluid chamber 44 to withdraw the blood sample from the patient into the second fluid chamber 60 and into intimate contact with the one or more sensors 114 for analysis. After the procedure is completed the operator may appropriately dispose of the sensor/syringe 40 and calibrator 10.

The above-described lost motion relationship of the piston 66 with respect to the actuator 48 also reduces the possibility of any loss fluid from the sensor/syringe 40 during use of disposal. As can be seen from the above description, the piston 66 should move in one direction only, namely, in a withdrawal mode and all the withdrawn calibration solution and blood sample remains in the syringe portion of 40. If the actuator 48 were inadvertently moved forward as if to expel fluid from the sensor/syringe 40, the actuator 48 would slidably move within the piston 66 at its first shaft portion 84 and the forward motion of the actuator 48 would not be transmitted to the piston 66.

Although the invention has been described in some detail by the foregoing, it is to be understood that many variations may be made therein without departing from the spirit and the scope thereof as defined by the appended claims.

We claim:

1. A fluid collection, sensing and calibrating apparatus, comprising:

calibrator having a base and holder portion adapted to hold at least one container containing calibration fluid, calibration container securely held in the holder of the calibrator, wherein the container is sealed to contain calibration fluid, fluid collection means adapted for fluid communication with the container but removable from the calibrator for fluid collection where the collector has a body portion defining a chamber at one end and has an actuating means slidable within the body portion at the other end to provide a variable volume for the chamber and having at the end of the chamber opposite the *actuating means a connecting means for fluid engagement with means for withdrawing calibration fluid, and at least one sensing means attached to the collector for fluid communication with the container and in fluid communication with the collection means so that when calibration fluid is withdrawn from the container by the actuating means of the collector and into the chamber the fluid contacts the sensor, and means for withdrawing calibration fluid by puncturing the seal of the container when the means is attached to the connecting means of the collector.

2. The apparatus of claim 1, wherein the at least one sensing means is located in a housing having a chamber for fluid where the housing engages the collector for fluid communication with the chamber of the collector at the distal end of the collector away from the slidable actuating means and the two chambers have a seal in between them and the slidable actuating means has a piercing member to puncture said seal.

3. The apparatus of claim 2, wherein the collector and sensing means and calibrator are in vertical arrangement.

4. The apparatus of claim 3, wherein the holder provides support for the vertical arrangement of the collector and sensing means.

5. The apparatus of claim 3, wherein the collection means is a syringe and the actuating means is a plunger of the syringe and the means for withdrawing the calibration fluid is a needle for attachment to the syringe and for piercing the seal of the container with the calibration fluid.

6. The apparatus of claim 5, wherein a seal is between the conduit of the housing and the container in the calibrator and the means for withdrawing the calibrant is a double ended needle fixedly engaged in an annular elastomeric holder that has a receiving means for the collector with the sensing means so that the needle can pierce both the seal of the container and the seal between the housing and the container.

7. In combination, a syringe having a body portion having first and second fluid communicating chambers with a first fluid seal therebetween, said first chamber defining a cylinder with a piston slidable therein, means for actuating said piston, said actuating means carrying a first seal puncturing means, said second chamber defining a housing for a sensing means and terminating in connecting means for fluid engagement with means for withdrawing a sample of fluid defining a connecting conduit in fluid communication with said second chamber, said connecting conduit sealed by a second fluid seal, sensing means disposed in said second chamber for sensing at least one analyte in the sample of fluid, and a calibrator for calibrating said sensing means, said calibrator having a body portion defining a cylinder open at one end for receiving at least a portion of said body portion of said syringe, a movable member carrying a second seal puncturing means that is slidable in said cylinder of said calibrator, and a sealed container containing calibration solution supported in the end of said cylinder of said calibrator opposite said opening.

8. The combination of claim 7, wherein said first fluid seal is adjacent to said piston with a centrally disposed, axially extending aperture in said piston, said first seal puncturing means is disposed at the end of said actuating means to puncture said first fluid seal and to operatively engage said piston to move said piston in said first chamber to draw said calibration solution from said container into said first chamber.

9. The combination of claim 8, wherein said actuating means is a reciprocal actuator reciprocally mounted in a spring biased sleeve slidably mounted on said syringe body portion, at one end thereof, said spring biased sleeve biasing said actuator to slidably move said engaged piston in said first chamber a first incremental distance to draw said calibration solution from said container into said second chamber into intimate contact with said sensing means.

10. The combination of claim 9, wherein said piston is seated on a seat provided at one end of said first chamber nearest said second chamber and said first seal puncturing means includes a puncturing head provided at the end of said reciprocal actuator.

11. The combination of claim 10, wherein said piston is resilient and said puncturing head is provided with a skirt portion and said puncturing head is urged into and through said aperture in said piston by said reciprocal actuator, said piston is captured on said reciprocal actuator, for movement therewith, by said portion.

12. The combination of claim 10 wherein reciprocal actuator is provided with a first shaft portion terminating at one end in a raised portion and at the other end in said skirt portion, said piston being slidably restrained on said shaft portion, by and between said skirt portion and said raised portion, for lost motion between said piston and said reciprocal actuator, whereby said piston will remain stationary when not engaged by said skirt portion or said raised portion.

13. The combination of claim 10 wherein reciprocal actuator is provided with a second shaft portion terminating at one end in a grasping means and at the other end in said raised portion, said second shaft portion being hollow and defining a cavity therein, there being at least one aperture in the wall of said second shaft portion having a porous fluid absorbent and expandable material disposed in said cavity for absorbing any fluid that may bypass said piston, said material expanding upon contact of any such fluid to seal said cavity from any fluid flow therethough.

14. The combination of claim 11 wherein said second seal puncturing means is a hollow double ended needle centrally disposed through said movable member and said movable member is urged toward said container by said syringe as said syringe and said calibrator are progressively moved, one relative to the other whereby said needle punctures said second fluid seal and said seal of said container.

15. The combination of claim 7, wherein said body portion of said calibrator and the portion of said body portion of said syringe defining said first chamber are circular in cross section.

16. The combination of claim 7, wherein the longitudinal axis of said syringe is coincident with the longitudinal axis of said calibrator.

17. The combination of claim 7, wherein said calibrator is provided with clamping means including a C-shaped portion which clampingly engages at least a portion of the exterior surface of said calibrator.

18. The combination of claim 17, wherein said clamping means includes a outwardly grasping means outwardly projecting from C-shaped portion for grasping and positionally holding said calibrator.

19. The combination of claim 17, wherein said clamping means includes a plurality of inwardly facing projections formed on the interior surface of said C-shaped portion and in registration with a plurality of slots provided in the wall of said calibrator for centrally aligning said syringe with respect to said calibrator.

20. The combination of claim 14, wherein said connecting means is a hub portion projecting from said syringe body for receiving a hypodermic needle or an arterial catheter for drawing said sample fluid, and wherein said second fluid seal is disposed at or near the open end of said connecting conduit that is in said hub, and wherein said movable member includes a centrally disposed cavity for receiving at least a portion of said hub portion, and wherein a portion of said needle centrally disposed in said cavity to puncture said second fluid seal.

21. The combination of claim 20, wherein said member includes at least one resilient finger terminating in a first outwardly projecting tab for lockable registration in a transversely extending slot in the wall of the calibrator body portion as said movable member is urged toward said container by said syringe to restrain the movement of said movable member when said hub portion is removed from said cavity.

22. The combination of claim 21, wherein said movable member includes at least one second outwardly projecting tab for registration in a longitudinally extending slot in the wall of the calibrator body portion to guide the slidable travel of said movable member as it is urged toward said container by said syringe.

23. The combination of claim 7, wherein said container is a glass vial seated and centrally disposed in said calibrator, the mouth of said vial being sealed by a puncturable cap.

24. The combination of claim 23, wherein said glass vial is seated and centrally received in a cup member, said cup member being centrally aligned in said calibrator by a plurality of inwardly facing projections formed on the interior surface of said calibrator.

25. The combination of claim 24, wherein said cup member is plastic and is sealingly received by said calibrator.

26. The combination of claim 11, wherein said syringe and said calibrator are manufactured from inexpensive material and are disposable after one use.

27. The combination of claim 26, wherein said syringe body portion, said calibrator body portion, said reciprocal actuator and said piston, are manufactured from plastic.

28. The combination of claim 1, wherein said sensing means is a electrode assembly and includes a means for connecting said electrode assembly to a signal processing means to process the output signal of said electrode assembly.

29. The combination of claim 28, wherein said sample fluid is blood.

30. The combination of claim 29, wherein said calibration solution has a predetermined pH, pO2 and pCO2 values for use in calibrating said electrode assembly.

31. A syringe having a body portion having first and second fluid communicating chambers with a first fluid seal therebetween, said first chamber defining a cylinder with a piston slidable therein, means for actuating said piston, said actuating means carrying a firs seal puncturing means, said second chamber defining a housing for a sensing means and terminating in connecting means for fluid engagement with means for withdrawing a sample of fluid defining a connecting conduit in fluid communication with said second chamber, said connecting conduit sealed by a second fluid seal, sensing means disposed in said second chamber for sensing at least one analyte in the sample of fluid.

32. The method of determining arterial pH, pCO2 and pO2 in whole blood using a disposable prepackaged syringe having a body portion having first and second fluid communicating chambers with a first fluid seal therebetween, said first chamber defining a cylinder with a piston slidable therein, means for actuating said piston, said actuating means carrying a first seal puncturing means, said second chamber defining a housing for a sensing means and terminating in connecting means for fluid engagement with means for withdrawing a sample of fluid defining a connecting conduit in fluid communication with said second chamber, said connecting conduit sealed by a second fluid seal, sensing means disposed in said second chamber for sensing pH, pO2 and pCO2 in the sample of whole blood and a calibrator for calibrating said sensing means, said calibrator having a body portion defining a cylinder open at one end for receiving at lest a portion of said body portion of said syringe, a movable member, carrying a second seal puncturing means, slidable in said cylinder of said calibrator, a sealed container containing calibration solution supported in the end of said cylinder of said calibrator opposite said opening, comprising the steps of:
  unpackaging the syringe and calibrator,
  progressively moving said syringe and said calibrator one relative to the other,
  puncturing the said first fluid seal, said second fluid seal and said seal of said sealed container containing calibration solution,
  aspirating the calibration solution from the container into contact with the sensing means,
  calibrating said sensing means,
  removing said syringe from said calibrator and attaching the syringe to a hypodermic needle or a arterial catheter,
  drawing of the whole blood,
  determining of arterial pH, pCO2 and pO2 in the withdrawn whole blood; and
  disposing of said syringe.

33. A fluid calibrator for calibrating a syringe having an electronic sensing means for sensing at least one analyte in the sample of fluid; said calibrator comprising:

body portion defining a cylinder open at one end for receiving at least a portion of the body of a syringe, movable member, carrying a seal puncturing means, slidable in said cylinder of said calibrator, sealed container containing calibration solution supported in the end of said cylinder opposite said opening, wherein said movable member is adapted to be fluidly coupled to and to be urged by the slidably received syringe toward said container whereby said seal puncturing means punctures the seal of said sealed container to achieve fluid communication between said container and the syringe for drawing said solution from said container into the syringe for calibrating the sensing means.

34. The fluid calibrator of claim 33, wherein said movable member includes at least one resilient finger terminating in a first outwardly projecting tab for lockable registration in a transversely extending slot in the wall of the calibrator body portion as said movable member is urged toward said container by said syringe to restrain the movement of said movable member when the syringe is removed from the movable member.

35. The fluid calibrator of claim 34, wherein said movable member includes at least one second outwardly projecting tab for registration in a longitudinally extending slot in the wall of the calibrator body portion to guide the slidable travel of said movable member as it is urged toward said container by said syringe.

36. The fluid calibrator of claim 33, wherein said container is a glass vial seated and centrally disposed in said calibrator, the mouth of said vial being sealed by a puncturable cap.

37. The fluid calibrator of claim 36, wherein said glass vial is seated and centrally received in a cup member, said cup member being centrally aligned in said calibrator by a plurality of inwardly facing projections formed on the interior surface of said calibrator.

38. The fluid calibrator of claim 37, wherein said cup member is plastic and is sealingly received by said calibrator.

39. The fluid calibrator of claim 33, wherein the seal puncturing means is a double-ended hollow needle.

* * * * *